United States Patent [19]

Lefevre et al.

[11] Patent Number: 5,232,857
[45] Date of Patent: Aug. 3, 1993

[54] REAGENT FOR USE IN AUTOMATIC ANALYZERS FOR DISTINGUISHER LEUKOCYTE SUB-POPULATIONS IN BLOOD SAMPLES

[75] Inventors: Didier Lefevre, Mantes la Ville; Nadine Voltas, Bordeaux; Henri Champseix, Montesson, all of France

[73] Assignee: ABX, Montpellier, France

[21] Appl. No.: 615,710

[22] Filed: Nov. 19, 1990

[30] Foreign Application Priority Data

Nov. 20, 1989 [FR] France .................. 89 15166

[51] Int. Cl.5 ............................ G01N 31/00
[52] U.S. Cl. .......................... 436/10; 436/17; 436/18; 436/63; 424/3; 424/7.1
[58] Field of Search ............. 436/10, 17, 18, 63; 435/29; 424/3, 7.1

[56] References Cited

U.S. PATENT DOCUMENTS 4,286,963  9/1981  Ledis et al. ................. 23/230 B

FOREIGN PATENT DOCUMENTS 0214613  3/1987  European Pat. Off. .
WO8404969  12/1984  PCT Int'l Appl. .
WO8505684  12/1985  PCT Int'l Appl. .
2077916  12/1981  United Kingdom .

OTHER PUBLICATIONS

Kass et al (1981) Am. J. Clin. Pathol. 76:810–12.

Primary Examiner—James C. Housel
Assistant Examiner—Maureen M. Wallenhorst
Attorney, Agent, or Firm—Birch, Stewart, Kolasch & Birch

[57] ABSTRACT

The present invention relates to a reagent and to a method of using the same for automatically determining at least one leukocyte sub-population from a total blood sample. Using this reagent, it is possible, in a single step, to lyse the erythrocytes through the action of saponin and SDS, as well as to ensure the differential staining of the leukocyte sub-populations, at the same time preserving the integrity and morphology of the cells, through the combined action of various components including chlorazol black, an alcohol, a surfactant and preserving agents. The reagent according to the invention can be applied to different types of automatic flow cytometry analyzers.

22 Claims, No Drawings

REAGENT FOR USE IN AUTOMATIC ANALYZERS FOR DISTINGUISHER LEUKOCYTE SUB-POPULATIONS IN BLOOD SAMPLES

BACKGROUND OF THE INVENTION

1. Field of the Invention

The present invention relates to the analysis of blood formulae by counting and discriminating between leukocyte sub-populations, and more particularly to a reagent and a method of using the same for determining, using flow cytometry, at least one leukocyte sub-population.

2. Description of Related Art

The importance, in making diagnoses, of precisely determining the different leukocyte populations has long been recognized. Indeed, the occurrence of abnormal leukocyte ratios can be correlated with that of certain diseases (immune responses, inflammatory reactions, the appearance of neoplasms or leukaemias, etc.).

The traditional methods of manual analysis, including physically separating the erythrocytes (by sedimentation or aggregation) and then differentially staining the cytoplasms and nuclei of the leukocytes and observing their morphology under the microscope, already permitted identification of all the types of leukocytes, i.e. the granulocytes (basophils, eosinophils and neutrophils and the agranulocytes (monocytes and lymphocytes). These methods yield reliable results, but they are time consuming, which makes them seldom transposable for determinations using automatic apparatus, or only with difficulty.

Different apparatus permitting automatic counting of leukocyte populations are already on the market, and various reagents and staining agents have been developed and adapted to suit the operating principles of such apparatus.

It is possible, for instance, to measure the sizes of the cells (after differential lysis of their cytoplasms), either by measuring variations in resistivity or by measuring optical diffraction; it is also possible to carry out specific staining (enzymatic or otherwise) of different cell types and measure the sizes and optical densities of the cells at different wavelengths.

One of the problems posed by automation is the possibility of confusion between erythrocytes and certain small-sized leukocytes, which is an artefact that did not occur with microscopic observation. Total lysis of the erythrocytes thus has to be ensured before the blood sample is put through the apparatus, at the same time preserving the integrity of the leukocytes. In addition, the reaction mixture has to include one or more reagents that will facilitate discrimination between the different types of leukocytes and their grouping into quite distinct zones on a histogram.

Patent WO 8505684 (Coulter Electronics Inc.) thus describes a group of reagents which ensure, in two stages, the specific lysis of the erythrocytes by saponin, and then the fixation (and thereby protection) of the leukocytes by glutaraldehyde. In addition, discrimination between the different types of leukocytes is favoured by the addition of a reagent such as phenoxy-2-ethanol; certain populations can also be specifically stained and identified by fluorescence. This efficient, reliable, but complex, process is particularly suitable for an apparatus of the Coulter Counter® type, as described in U.S. Pat. No. 3,502,974.

Other methods, described, for example, in U.S. Pat. No. 3,740,143, which are particularly suitable for Technicon ® apparatus, involve several reactions conducted in parallel, each revealing a cell type, these specific reactions being preceded or followed, moreover, by an erythrocyte lysis treatment, and possibly a leukocyte fixation treatment. The specific reactions include conventional histological staining (such as "neutral red" for the basophilic cells) and enzymatic staining (such as revealing the peroxidase content of the eosinophilic and neutrophil cells using chloronaphthol, or the lipase content of the monocytes using naphthol butyrate).

Generally speaking, detailed, reliable analyses can only be carried out using highly complex apparatus and methods that comprise several different stages, conducted using different reagents. Owing to their complexity, the cost of such analyses is very high and, for the purposes of routine diagnoses, it is always desirable to simplify the process, while preserving the same discrimination power and the same degree of reliability.

SUMMARY OF THE INVENTION

The Applicant has thus developed a composition which, in a single reaction, permits the lysis of the erythrocytes, the protective fixation of the leukocytes and the staining of the eosinophilic cells, as well as very efficient separation of the different leukocyte sub-populations on a histogram. The method of using the composition according to the invention is particularly swift and is suitable for any type of automatic counting apparatus.

DETAILED DESCRIPTION OF THE INVENTION

More particularly, the reagent according to the present invention comprises, on one hand, at least one erythrocyte lysing agent and, preferably, a saponin and sodium dodecyl sulphate (SDS), and, on the other hand, an agent capable of differentially staining the various leukocyte populations and, in particular, chlorazol black at a concentration of between 50 and 650 mg/l. The other constituents of the reagent which are designed to preserve the natural integrity and morphology of the cells and improve discrimination of the cells by optical detection, comprise at least one physiological salt to maintain the pH between 7.0 and 12.0, a tertiary or quaternary ammonium salt, a primary, secondary or tertiary alcohol, a surfactant, a cell structure preserving agent and an alkyleneglycol.

Chlorazol black (also known as Erié black or formic black) is a conventional reagent, used since 1937 in plant histology (Cannon, H. G., *Nature*, 139,549) for the specific staining of eosinophilic cells, for observation under the microscope. (This reagent and its method of use are described by M. Piette, *Ann. Biol. Clin.* 1961, 19, 729–734 and K. Lawrence, *Am. J. Clin. Pathol.* 1981, 76, 810–812).

The usual conditions of use for chlorazol black (650 mg/l) are not at all suitable for detection with an automatic photodiode apparatus, the eosinophilic cells being far too black and the other cells appearing completely transparent. New conditions of use have been developed, at the same time reducing the reagent concentration and increasing the temperature at which the reaction is carried out on the blood sample.

The reagent according to the invention thus preferably contains a chlorazol black concentration of less than 100 mg/l. The Applicant has observed that, under these conditions, the eosinophilic cells are clearly stained and, furthermore, the other granulocytes are fixed and clearly discriminated. Slight staining of all the leukocyte populations occurs, but it disappears if the reaction duration is prolonged.

In looking for the best balance between the different constituents of the reagent, the Applicant has noted that the addition of glutaraldehyde in an aqueous solution improved discrimination between the cell sizes, when measurement is carried out by resistivity. However, the glutaraldehyde increases the size of the stromas resulting from the lysis of the erythrocytes. This artefact can advantageously be corrected by adding SDS, which accelerates the destruction of the erythrocytes, at concentrations that do not damage the morphology of the leukocytes. Furthermore, the addition of a tertiary or quaternary ammonium salt further improves discrimination between the cell sub-populations and also contributes to the destruction of the erythrocyte stromas. Dodecyltrimethylammonium chloride can be used advantageously. Equivalent results are obtained with bromides and iodides; similarly, use can be made of tertiary or quaternary salts, the preferred alkyl radicals of which are $C_{12}$ and $C_{14}$. A dodecyldi(or tri)methylammonium halogen (Cl, Br or I) or a tetradecyldi(or tri)-methylammonium, alone or in combination, will thus be chosen.

The reagent according to the invention also contains a surfactant chosen, for example, from the family of polyoxyethylene sorbitan esters and, more particularly, polyoxyethylene sorbitan monolaurate (Tween 20®), and polyoxyethylene sorbitan monooleate (Tween 80®).

Furthermore, the addition of an alkyleneglycol, which also has a preserving effect on the cell structures, has, above all, a favourable effect in the case of optical reading as it limits the diffraction of the medium.

Thus, according to a preferred form of embodiment of the invention, the reagent includes the following constituents:

a saponin, at a concentration of between 100 and 700 mg/l,

SDS, at a concentration of between 100 and 400 mg/l, chlorazol black, preferably at a concentration of less than 100 mg/l, a physiological salt or a mixture of physiological salts including from 1.3 to 9.5 g/l of sodium chloride, from 15 to 20 g/l of sodium sulphate, from 400 to 700 mg/l of sodium carbonate, at least one tertiary or quaternary ammonium salt, in a final ratio of 0.03 to 0.10% by volume, a primary, secondary or tertiary alcohol and, preferably, isopropyl alcohol in a final ratio of 2 to 13% by volume, a polyoxyethylene sorbitan ester in an aqueous solution, in a final ratio of 0.2 to 2% by volume, glutaraldehyde or formaldehyde in an aqueous solution, in a final ratio of 0.1 to 0.8% by volume, ethyleneglycol or propyleneglycol, in a final ratio of 2 to 13% by volume.

The invention also relates to a method of using this reagent in order to determine, in an automatic flow cytometry analyzer, at least one leukocyte sub-population. The method according to the present invention includes contacting the blood sample to be studied with a reagent, in a thermostatically controlled chamber, at a temperature of between 20° and 80° C. and, preferably, between 40° C. and 65° C., for a period of less than 20 seconds.

The method then includes detecting and discriminating between leukocytes by measuring the variations in absorbance or resistivity, or a combination of the two, using a suitable analyzer, and recording these measurements in the form of matrixes or histograms permitting visual representation of the contours representative of the distribution of the leukocyte sub-population.

The following example illustrates a form of embodiment of the invention without, however, restricting the scope thereof.

EXAMPLE

The following concentrations of the various constituents are calculated for the preparation of one liter of reagent:

| | |
|---|---|
| saponin | 650 mg |
| SDS | 200 mg |
| chlorazol black | 65 mg |
| sodium chloride | 5.144 g |
| sodium sulphate | 17.4 g |
| sodium carbonate | 650 mg |
| ammonium salt | 0.3 ml |
| isopropyl alcohol | 130 ml |
| Tween 80 | 13 ml |
| glutaraldehyde | 4 ml |
| propyleneglycol | 130 ml |
| distilled water for adjustment to the final volume of | 1 liter. |

The reagent is used, for example, in any other type of device for automatically counting leukocyte populations.

The apparatus is set to contact a sample of 25 μl of total blood and 1 ml of reagent. This mixture is produced in a thermostatically controlled chamber at a temperature of between 40° and 65° C.

What is claimed is:

1. A reagent for determining, in an automatic flow cytometry analyzer, at least one leukocyte sub-population, wherein said reagent comprises the following constituents:

at least one erythrocyte lysing agent chlorazol black at least one physiological salt at least one tertiary or quaternary ammonium salt an alcohol a surfactant a preserving agent an alkyleneglycol.

2. The reagent according to claim 1, wherein said at least one erythrocyte lysing agent is at least one member selected from the group consisting of a saponin and sodium dodecyl sulphate.

3. The reagent according to claim 2, wherein said at least one erythrocyte lysing agent is saponin at a concentration of between 100 and 700 mg per liter of reagent.

4. The reagent according to claim 2, wherein said at least one erythrocyte lysing agent is sodium dodecyl sulphate at a concentration of between 100 and 400 mg per liter of reagent.

5. The reagent according to claim 1, wherein the concentration of said chlorazol black is between 50 and 650 mg per liter of reagent.

6. The reagent according to claim 5, wherein the concentration of said chlorazol black is less than 100 mg/l.

7. The reagent according to claim 1, wherein said at least one physiological salt is selected from the group consisting of sodium chloride, sodium sulphate, and sodium carbonate in order to maintain the pH of said reagent between 7.0 and 12.0.

8. The reagent according to claim 7, wherein said at least one physiological salt is sodium chloride at a concentration between 1.3 and 9.5 g per liter of reagent.

9. The reagent according to claim 7, wherein said at least one physiological salt is sodium sulphate at a concentration between 15 and 20 g per liter of reagent.

10. The reagent according to claim 7, wherein said at least one physiological salt is sodium carbonate at a concentration between 400 and 700 mg per liter of reagent.

11. The reagent according to claim 1, wherein said at least one tertiary or quaternary ammonium salt is present in a final ratio of 0.03% to 0.10% by volume of said reagent.

12. The reagent according to claim 1, wherein said alcohol is selected from the group consisting of a primary, a secondary, and a tertiary alcohol, in a final ratio of 2 to 13% by volume of said reagent.

13. The reagent according to claim 1, wherein said surfactant is a polyoxyethylene sorbitan ester in aqueous solution, in a final ratio of 0.2 to 2% by volume of said reagent.

14. The reagent according to claim 1, wherein said preserving agent is selected from the group consisting of glutaraldehyde and formaldehyde in aqueous solution, in a final ratio of 0.1 to 0.8% by volume of said reagent.

15. The reagent according to claim 1, wherein said alkyleneglycol is selected from the group consisting of ethyleneglycol and propyleneglycol, in a final ratio of 2 to 13% by volume of said reagent.

16. The reagent according to claim 11, wherein said at least one ammonium salt has an alkyl radical of $C_{12}$ or $C_{14}$.

17. The reagent according to claim 11, wherein said at least one ammonium salt is an iodide, bromide, or chloride.

18. The reagent according to claim 11, wherein said at least one ammonium salt is at least one member selected from the group consisting of a dodecyldimethylammonium halogen, a dodecyltrimethylammonium halogen, a tetradecyldimethylammonium halogen, and a tetradecyltrimethylammonium halogen.

19. The reagent according to claim 18, wherein said at least one ammonium salt is dodecyltrimethylammonium chloride.

20. The reagent according to claim 13, wherein said polyoxyethylene sorbitan ester is a member selected from the group consisting of polyoxyethylene sorbitan monolaurate and polyoxyethylene sorbitan monooleate.

21. The reagent according to claim 1, wherein said reagent comprises the following constituents:

a saponin, at a concentration of between 100 and 700 mg/l sodium dodecyl sulphate, at a concentration of between 100 and 400 mg/l chlorazol black, at a concentration of less than 100 mg/l at least one physiological salt selected from the group consisting of sodium chloride at a concentration of between 1.3 to 9.5 g/l, sodium sulphate at a concentration of between 15 to 20 g/l, and sodium carbonate at a concentration of between 400 to 700 mg/l at least one tertiary or quaternary ammonium salt, in a final ratio of 0.03 to 0.10% by volume of said reagent isopropyl alcohol in a final ratio of 2 to 13% by volume of said reagent a polyoxyethylene sorbitan ester in aqueous solution, in a final ratio of 0.2 to 2% by volume of said reagent glutaraldehyde or formaldehyde in aqueous solution, in a final ratio of 0.1 to 0.8% by volume of said reagent, and ethyleneglycol or propyleneglycol, in a final ratio of 2 to 13% by volume of said reagent.

22. The reagent according to claim 21, wherein said reagent comprises the following constituents:

saponin, 650 mg
sodium dodecyl sulphate, 200 mg
chlorazol black, 65 mg
sodium chloride, 5.144 g
sodium sulphate, 17.4 g
sodium carbonate, 650 mg
ammonium salt, 0.3 ml
isopropyl alcohol, 130 ml
polyoxyethylene sorbitan monooleate, 13 ml
glutaraldehyde, 4 ml
propyleneglycol, 130 ml
distilled water to a final volume of 1 liter.

* * * * *

UNITED STATES PATENT AND TRADEMARK OFFICE
CERTIFICATE OF CORRECTION

PATENT NO. : 5,232,857
DATED : August 3, 1993
INVENTOR(S) : D. Lefevre, et al.

It is certified that error appears in the above-indentified patent and that said Letters Patent is hereby corrected as shown below:

On the title page, item [54] and column 1, line 3, change "DISTINGUISHER" to --DISTINGUISHING--.

Signed and Sealed this

Twenty-first Day of March, 1995

Attest:

BRUCE LEHMAN

*Attesting Officer*   *Commissioner of Patents and Trademarks*